United States Patent [19]
Noren et al.

[11] Patent Number: 5,697,957
[45] Date of Patent: Dec. 16, 1997

[54] ADAPTIVE METHOD AND APPARATUS FOR EXTRACTING AN EVOKED RESPONSE COMPONENT FROM A SENSED CARDIAC SIGNAL BY SUPPRESSING ELECTRODE POLARIZATION COMPONENTS

[75] Inventors: Kjell Noren, Solna; Hans Strandberg, Sundbyberg, both of Sweden

[73] Assignee: Pacesetter AB, Solna, Sweden

[21] Appl. No.: 705,272

[22] Filed: Aug. 29, 1996

[51] Int. Cl.$^6$ .................................................. A61N 1/37
[52] U.S. Cl. ........................... 607/28; 128/708; 128/901
[58] Field of Search ........................ 607/7, 9, 11, 28; 128/697, 708, 901

[56] References Cited

U.S. PATENT DOCUMENTS

| | | | |
|---|---|---|---|
| 5,172,690 | 12/1992 | Nappholz et al. | 607/9 |
| 5,417,718 | 5/1995 | Kleks et al. | 607/28 |
| 5,431,693 | 7/1995 | Schroepel | 607/28 |
| 5,458,623 | 10/1995 | Lu et al. | 607/28 |
| 5,607,457 | 3/1997 | Schüller | 607/9 |

OTHER PUBLICATIONS

"Morphologie Of The Endocardial Ventricular Evoked Response At Variable External Stimulation Parameters," eichstaedt et al, Herzschrittmacher, vol. 15, No. 4 (1995) pp. 184–188.

"Analysis Of The Morphology Of The Unipolar Endocardial Paced Evoked Response" Brouwer et al, PACE, vol. 13, Mar. 1990, pp. 302–313.

"The Ventricular Intracardiac Unipolar Paced–Evoked Potential In An Isolated Animal Heart," Economides et al, PACE, vol. 11, Feb. 1988, pp. 203–213.

Abstract of "A Model Of the Polarization Dependent Impedance," Uhrenius, Master Thesis, The Royal Institute of Technology, Stockholm 1995.

*Primary Examiner*—Jeffrey R. Jastrzab
*Attorney, Agent, or Firm*—Hill, Steadman & Simpson

[57] ABSTRACT

In a method and apparatus for suppressing electrode polarization components in a sensed cardiac signal, the sensed cardiac signal is added to either a differentiated or autocorrelated sensed cardiac signal and a difference is formed between the original sensed cardiac signal and the autocorrelated or differentiated signal, thereby extracting an evoked response component from the sensed cardiac signal, the evoked response component otherwise being overshadowed by the much higher-amplitude polarization component.

21 Claims, 16 Drawing Sheets

Exponential Decay and ACF Normalized at t=0

Difference of Normalized signals

Evoked Response, Amplitude=1mV

Response of a Pacemaker Sensing Amplifier Filter

Enlarge Detail of Pacemaker Filter Response

Signal Extracted by Signal Processing

Unipolar Endocardial Evoked Response

Amplitude Spectrum of Evoked Response

Evoked Response with a Notch

Signal Extracted by Signal Processing

Evoked Response, (raw)

Sum of Polarization, Bias, Drift and Evoked Response. (Raw)

Signal Extracted by Signal Processing

Evoked Response, (raw)

Sum of Polarization, Bias, Drift and Evoked Response. (Raw)

Signal Extracted by Signal Processing

Evoked Response, (raw)

Sum of Polarization, Bias, Drift and Evoked Response. (Raw)

Signal Extracted by Signal Processing

Evoked Response. (Raw)

Sum of Polarization, Bias, Drift and Evoked Response. (Raw)

5,697,957

ADAPTIVE METHOD AND APPARATUS FOR EXTRACTING AN EVOKED RESPONSE COMPONENT FROM A SENSED CARDIAC SIGNAL BY SUPPRESSING ELECTRODE POLARIZATION COMPONENTS

BACKGROUND OF THE INVENTION

1. Field of the Invention

The present invention is directed to a method and apparatus for identifying an evoked response component contained within a sensed cardiac signal, the evoked response component being overshadowed by the much stronger electrode polarization components. More particularly, the invention is directed to an adaptive method and apparatus wherein the evoked response component is extracted from the sensed cardiac signal by signal processing which suppresses the electrode polarization components.

2. Description of the Prior Art

After the delivery of a stimulation pulse by an implanted pacemaker, the pacemaker is typically switched from a stimulation pulse emitting mode to a sensing or measuring mode, in order to determine whether the heart has reacted (contracted) to the stimulation pulse. If the heart has contracted as a result of the stimulation pulse, this is known as "capture." The existence of capture means that the amplitude of the stimulation pulse was large enough to result in the desired response. It is advantageous to minimize the amplitude of stimulation pulses in order to conserve energy in the implanted pacemaker battery, to increase the battery life. Many pacemakers employ an Autocapture™ function in order to periodically or continually adjust the stimulation pulse energy to a value which just barely achieves capture, plus an added safety margin.

The signal component representing an evoked response, however, is of much lower magnitude than other signal components which are unavoidably contained in the sensed signal. The evoked response component will typically be of a relatively low amplitude, in the range of a few millivolts. The dominant components of the sensed signal consist of a decreasing polarization voltage, having a magnitude in the volt range. This polarization voltage will be particularly dominant, for example, when high electrode polarization is present, which occurs when a new pacemaker is implanted and is connected to an old (previously implanted) unipolar electrode which has been in place in the patient for several years.

The sensed signal is the sum of these two components, and the unwanted signal component arising due to the polarization voltage can be many times larger in magnitude than the desired (evoked response) component.

A simplified model which is often used to represent the polarization voltage $U_P$ is that of the exponential discharge of a capacitor through a resistor. As is well known, such a circuit has a time constant $\tau$ which is the product RC. The initial voltage $U_O$ across the capacitor is equal to the amplitude of the stimulation pulse, and therefore the polarization voltage has the form:

$$U_P = U_O e^{-\frac{t}{\tau}}$$

This is a simplified model. A more detailed analysis shows that the value $\tau$ is not really constant over time. This can be due to external effects on the patient and/or the implanted pacing system. Another factor which changes the value of $\tau$ is the extent to which tissue ingrowth occurs around the electrode tip after implantation. The position of the patient's body, i.e., whether the patient is prone or standing, can effect the polarization behavior.

Moreover, the polarization is not linear with respect to the stimulation voltage. Comparing stimulation in the atrium and in the ventricle, it is often found that the polarization in the atrium is larger than in the ventricle. Detection of an evoked response in the atrium is therefore more difficult than in the ventricle. The sensed cardiac component in the signal is also highly dependent on the position of the electrode in the atrium. A shifting in the positioning of the electrode by even a few millimeters in the atrium can result in a change by a factor of 10 in the amplitude of the measured IECG signal. If sensing for autocapture purposes is undertaken in atrium, there is no need to deliver a backup stimulation pulse to the atrium within a certain time in the event that a missing response is detected. A precondition for this, however, is that contractions are present in the ventricle, as is the situation in a DDD system with capture sensing taking place in the ventricle. Missing contractions in the atrium for several beats is not severe in this situation.

It would be a significant advantage if the evoked response could be detected in a similar manner in all electrode systems and in all pacing systems, i.e., unipolar, bi-polar, old and new electrode types, etc. One approach which currently has been taken to improve the capability of detecting the evoked response is to try to reduce the amplitude of the polarization component by developing low polarization electrodes. Such low polarization electrodes have other drawbacks associated therewith, and if effective signal processing methods to extract the evoked response from the overshadowing polarization components could be devised, this would reduce or avoid the need for low polarization electrodes.

Another known manner of decreasing the polarization is to emit a pulse of the opposite polarity (discharge pulse) immediately after the stimulation pulse. Other configurations of pulse trains are also known. This approach, however, does not insure that the detection problems will be solved, particularly in the atrium. The Microny® pacemaker commercially available from Pacesetter uses separate sensing of the IECG on the ring of a bipolar electrode in order to avoid saturation of the sensing amplifier. Another approach uses two stimulation pulses produced close to each other in time. The second pulse may, for example, be emitted 100 ms after the first pulse. The first pulse stimulates the heart and thus will produce (if successful), the polarization signal plus an evoked response component, but the heart is incapable of producing another evoked response within such a short time, and therefore the second pulse will contain only the polarization signal. The polarization signal by itself can be stored in a memory, and is subtracted from the signal containing both the polarization signal and the evoked response component.

SUMMARY OF THE INVENTION

It is an object of the present invention to provide a method and apparatus for extracting an evoked response component from a sensed signal obtained from an implanted medical device solely by signal processing, i.e., without the generation of special pulse trains or the use of special electrodes. It is a further object of the present invention to provide such a method and apparatus which are suitable for use with every electrode system, i.e., both with unipolar and bipolar electrode configurations. This means that sensing takes place using the same electrode as for stimulation or via another electrode surface, for example, a ring. The most difficult situation encountered is sensing in the atrium using a unipolar electrode, wherein sensing occurs between the electrode tip disposed in the atrium and the pacemaker housing, serving as the indifferent or return electrode. It is an object of the present invention to provide a method and apparatus wherein even under this most difficult of situations, the evoked response component can be reliably extracted from the sensed signal.

The above objects are achieved in accordance with the principles of the present invention in a method and apparatus wherein an electrical signal, such as a stimulation pulse, is delivered in vivo to a heart, and electrical activity in the heart is sensed after delivery of the signal, thereby obtaining a sensed cardiac signal. In one embodiment of the invention, an autocorrelation function is applied to the sensed cardiac signal and the autocorrelated signal and the sensed cardiac signal are then normalized relative to each other. A difference is then formed between the normalized sensed cardiac signal and the normalized autocorrelation signal, thereby extracting the evoked response component.

In this embodiment, sensing may take place in a data collection window, and the autocorrelation function is applied in a calculation window, which is a portion of the data collection window. The sensed cardiac signal can be subjected to anti-aliasing filtering, and thereafter selecting the data collection window. It is also possible to pre-process the sensed cardiac signal in the data collection window, with the pre-processed signal then being used as the sensed cardiac signal in the normalizing and difference forming. The pre-processing may be, for example, taking the first derivative of the sensed cardiac signal, or may be high pass filtering.

Normalization of the sensed cardiac signal and the autocorrelated signal, may, for example, be undertaken by identifying respective maxima in these two signals, and then setting these maxima to a common value, for example, one. In this embodiment, data is collected during a period of interest, and the collected data are then subsequently processed.

The method and apparatus, however, can also be realized using realtime processing. In the second embodiment, the sensed cardiac signal is low pass filtered, and is subsequently differentiated. The undifferentiated sensed signal and the differentiated sensed signal are then summed, with the resulting sum being amplified. The amplification can be controlled to minimize the polarization influence. The amplified, summed signal can then be supplied to a comparator for signal level detection. If desired, the summed and amplified signal, before comparison, can be differentiated. The output of the level detection stage indicates whether an evoked response component was contained in the original signal, and this level detection result can then be supplied to the pacemaker logic circuitry for suitable use.

The second embodiment has the advantage of being easy to realize with discrete circuit components, but has the drawback that the cancellation of the polarization signal is not perfect when, as noted above, the value τ is not constant over time. The second embodiment is sufficiently accurate for many purposes, however, and can be particularly useful when the amplifier settings can be tuned adaptively to achieve the best attenuation of the polarization signal, such as by means of internally programmed settings, or settings programmed via telemetry by means of an external programmer.

The first embodiment has the advantage of a highly effective cancellation of the unwanted polarization signal, but it has the drawback that the final result, i.e., an indication of whether an evoked response has occurred, is obtained later than the time which is needed for the generation of a backup stimulation pulse. This drawback can be compensated, however, by using a suitable sequence of changing stimulation pulse amplitudes. For example, after a first sub-threshold pulse, no backup pulse is delivered because the autocapture detection result is obtained too late. The autocapture detection according to the first embodiment continues to operate, however, and the next stimulation pulse is generated with a slightly increased amplitude, followed by delivery of a backup pulse after 60 ms. The computing according to the first embodiment, using data obtained following the second pulse, is then undertaken after delivery of the back up pulse. The amplitude increase and "blind" delivery of backup pulses continues until enough stimulation margin is achieved, at which point no further backup pulses are delivered. Thus, a full monitoring of the stimulation can be accomplished safely.

It is also possible to employ a mix of the two embodiments, for example, undertaking preliminary detection with mathematical reduced polarization to determine whether a back-up pulse should be delivered, followed by post-processing with a high accuracy to determine the stimulation amplitude.

DESCRIPTION OF THE PREFERRED EMBODIMENTS

Figure 1:
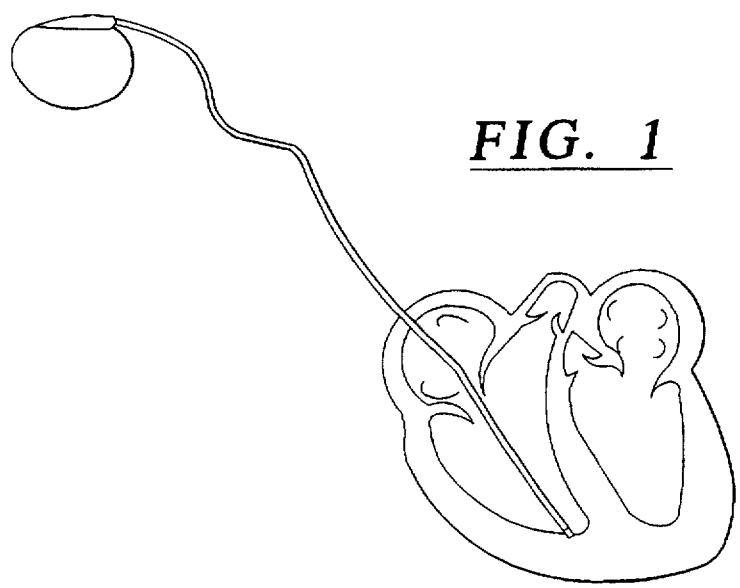
FIG. 1 is a schematic illustration showing a pacemaker, constructed and operating in accordance with the principles of the present invention, having a unipolar lead with the electrode thereof disposed in the ventricle of a heart.

FIG. 1 shows a typical unipolar system for pacing a human heart, in a VVI configuration with the electrode disposed in the ventricle. The circuitry disclosed herein can be contained in the pacemaker housing. The method and apparatus disclosed herein are also suitable for use in other types of pacing configurations, such as a DDD system, which has an electrode in the atrium as well as in the ventricle. In the VVI configuration of FIG. 1, stimulation and sensing takes place between the electrode tip and the metallic pacemaker housing (can). Typically, the cardiac signal component will be approximately ten times smaller in the atrium compared to the ventricle.

Figure 2:
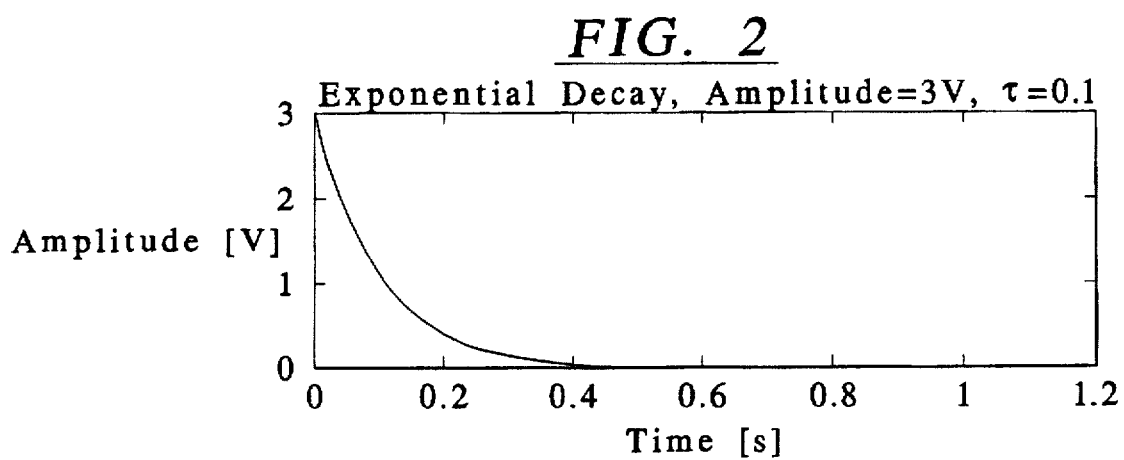
FIG. 2 shows a typical discharge curve using the above identified RC circuit model.

For explaining the method and apparatus of the invention, FIG. 2 shows a typical discharge curve based on the above discussed exponential decay model. The discharge curve in FIG. 2 ends at an amplitude of 3 V, and decreases with a time constant of 100 ms. The amplitude in the exemplary curve shown in FIG. 2 decreases to 7 mV after 0.6 seconds. This signal represents a simple model of the polarization (not to scale) decrease in the absence of a fast discharge pulse. Because the stimulation pulse emitted by the pacemaker is negative, the polarization is negative, however, it is shown as being positive in FIG. 2, and this convention will be adopted for all of the other figures.

Figure 3:
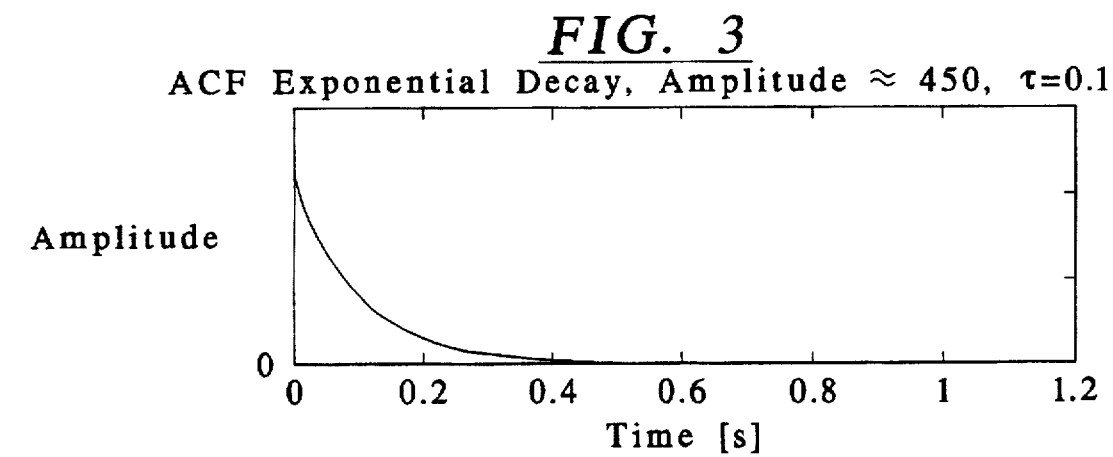
FIG. 3 shows the autocorrelation function of the curve of FIG. 1.

The autocorrelation signal for the exponential decay signal of FIG. 2 is shown in FIG. 3. Depending on the particular autocorrelation calculation algorithm which is used, slightly different amplitudes may result, (hence the vertical axis is only generally identified as representing amplitude, but with no units or divisions being shown). The important factor, however, is that the autocorrelation signal is also an exponential function, and the time constant is the same as for the original signal. This is always the case, which is the basis for the self-adapted signal processing method and apparatus disclosed herein.

Figure 4:
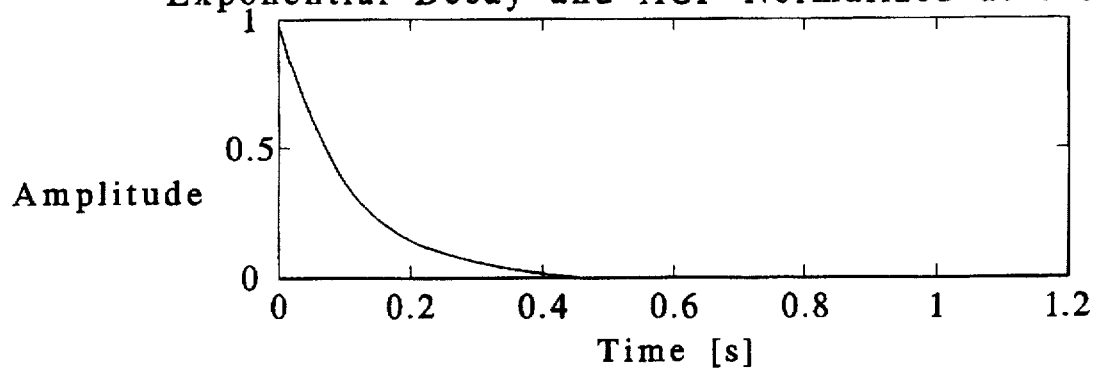
FIG. 4 shows the exponential decay curve of FIG. 2 and the autocorrelation function of FIG. 3 normalized at t=0.
Figure 5:
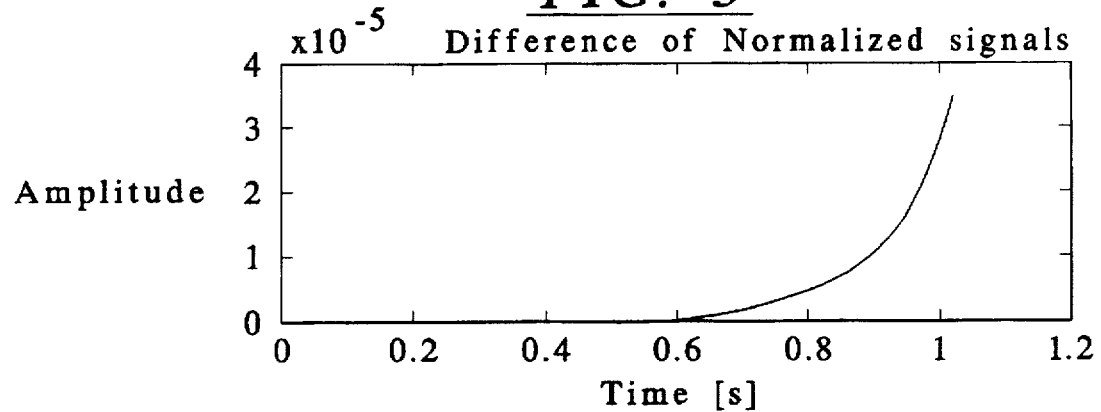
FIG. 5 shows the difference between the normalized signals.

By normalizing the two signals shown in FIG. 2 and FIG. 3, for example by setting the amplitude=1 at times t=0, the curve shown in FIG. 4 is obtained. Because of the amplitude scale, the slight differences between the two signals cannot be seen in FIG. 3, however, this difference is shown in FIG. 5, wherein the amplitude scale is appropriate for making this difference apparent.

Figure 6:
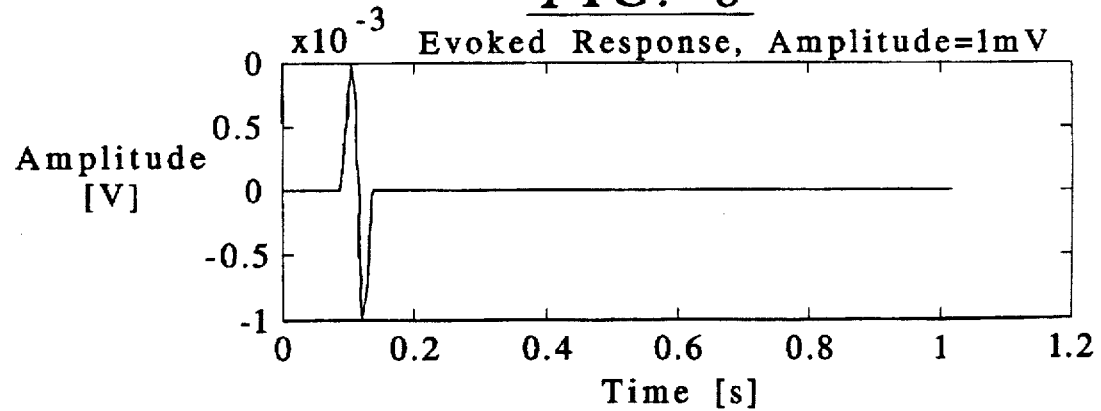
FIG. 6 is an example of an evoked response signal of the type it is desired to extract from the sensed signal.
Figure 7:
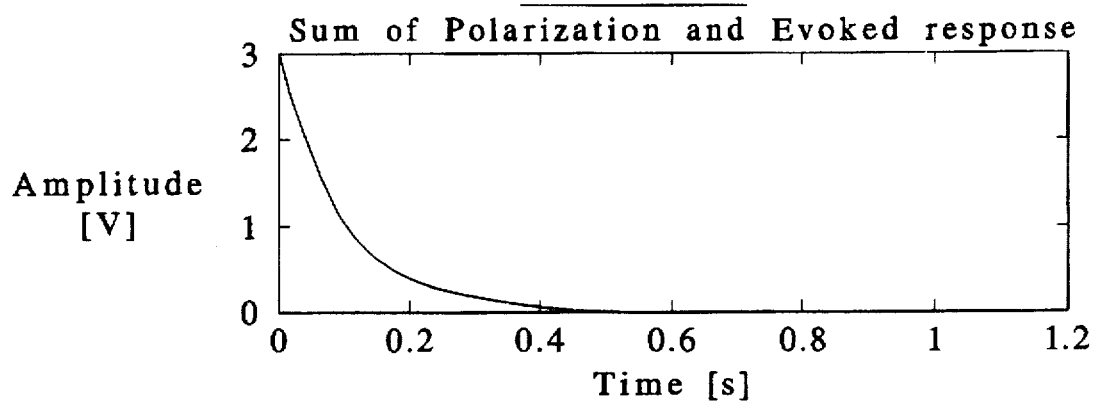
FIG. 7 shows the sum of the polarization and evoked response in the sensed signal.

The sequence shown in FIGS. 2, 3 and 4 therefore demonstrates the general basis, using the aforementioned exponential decay model, showing how the final difference signal is obtained, and showing how the technique is used to extract a signal having an extremely small component from a signal which, in totality, has components which overshadow the small amplitude component. FIGS. 6–9 illustrate the method using a test signal, shown in FIG. 6, representing an evoked response of the type which it is desired to extract. The test signal shown in FIG. 6, however, does not represent a true evoked response, since the peaks in the signal shown in FIG. 6 occur too late after time t=0, which is the time at which a stimulation pulse is assumed to have occurred. Typically, a true evoked response will occur approximately 50 ms after the stimulation pulse.

Figure 8:
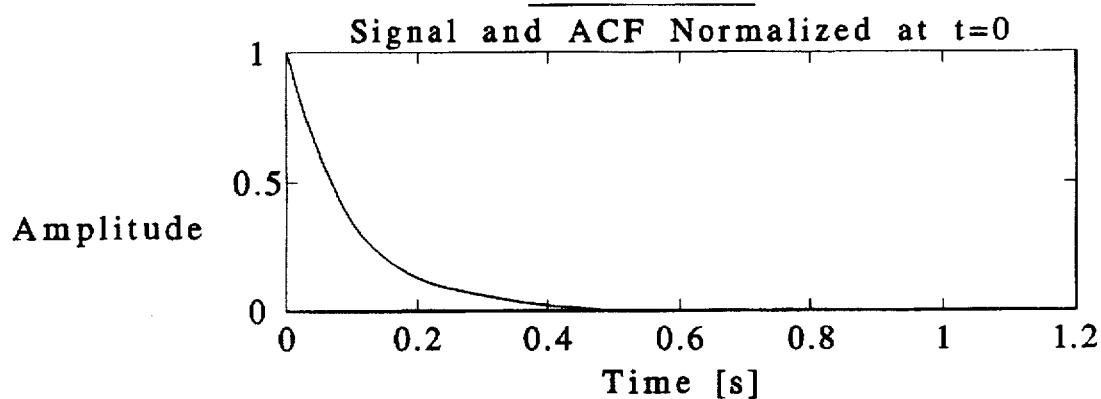
FIG. 8 shows the sensed signal and the autocorrelation function thereof normalized at t=0.
Figure 9:
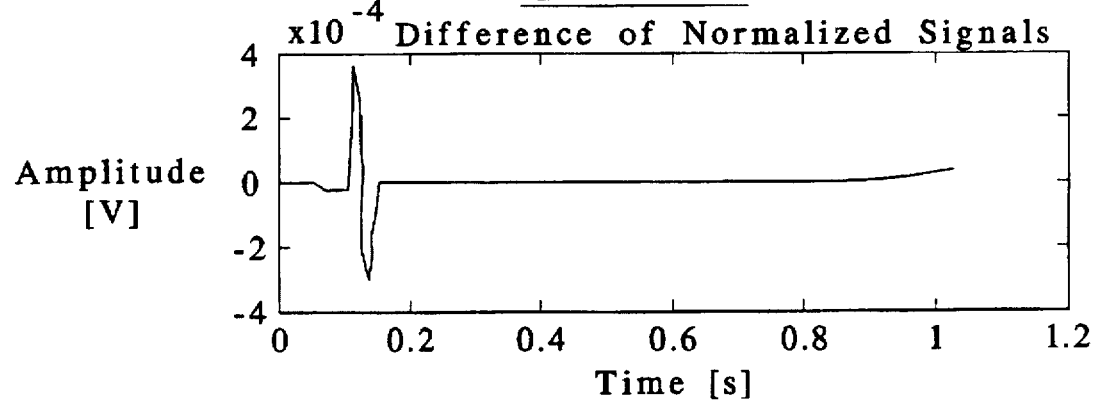
FIG. 9 shows the difference between the normalized signals in accordance with the invention.

The technique using the test signal shown in FIG. 6 will be described, again using the exponential decay model curve of FIG. 2. In this case, the signal which is actually detected would be the sum of the curves shown in FIGS. 2 and 6, which is shown in FIG. 7, but once again because of the relatively high amplitude scale, the details of the evoked response signal cannot be discerned. As described above, the signal shown in FIG. 7 is subjected to an autocorrelation function, and the original signal and the autocorrelated signal are then normalized at t=0, resulting in the curve shown in FIG. 8. Thereafter, the difference between the normalized original signal and the normalized autocorrelation function is calculated, the remainder being shown in FIG. 9, which clearly shows the extracted evoked response component. The signal shown in FIG. 9 looks very similar to the original signal, but it is actually an autocorrelated version of the original signal. The autocorrelation function calculation is a linear operation, which means that the normalized autocorrelation signal shown in FIG. 8 is the sum of the exponential component and the component arising from the cardiac signal. The morphology for the detected signal can therefore be different from the original signal, however, the frequency content will be the same in the two signals.

Figure 10:
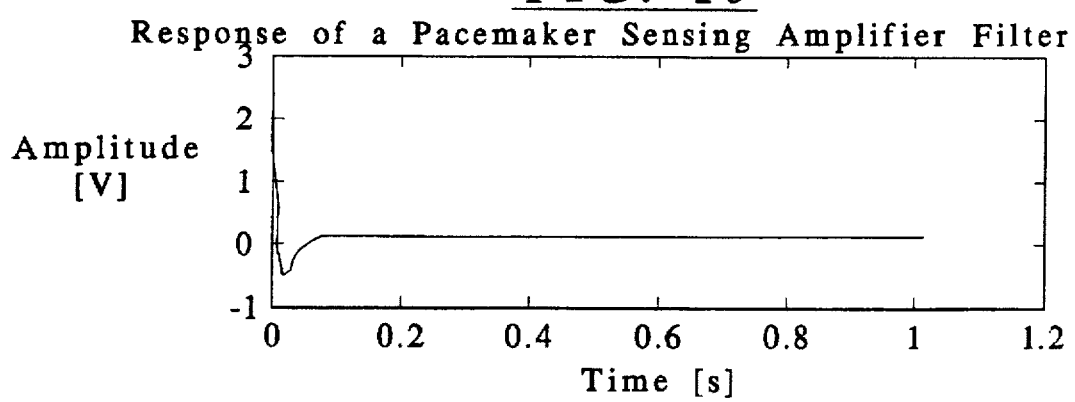
FIG. 10 shows the response of a typical pacemaker sensing amplifier filter.
Figure 11:
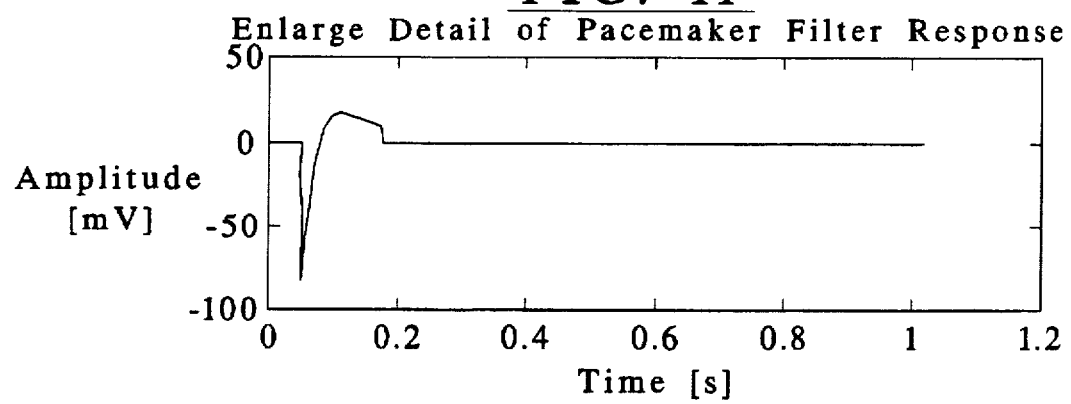
FIG. 11 shows an enlarged detail of the pacemaker filter response of FIG. 10.

For comparison purposes, FIGS. 10 and 11 show an example using the response of a typical pacemaker amplifier. The filter response shown in FIG. 10 is very similar to that in the pacemaker amplifier in the Microny® commercially available from Pacesetter, but with the gain set equal to one.

A magnification of the curve in the area of interest does not improve the clarity of the situation, as can be seen in FIG. 11. The large negative portion is an artifact dependent on the input filter transient, and the signal which is sought is substantially invisible, even in the magnified curve shown in FIG. 11.

The simple model described above using only one exponential function is limited. If a constant level is added to this signal (i.e., an offset) the possibility for accurate detection is significantly decreased. In clinical situations, many types of drifts also arise. An effective approach, however, is to model the polarization as a sum of exponential functions with different time constants. The range for these time constants is from very fast (such as less than 1 ms), intermediate (tens of ms) and longer (greater than 100 ms). The most interesting of these ranges are the fast and intermediate time constants. An autocorrelation function calculated from a signal with two time constants shows a small "hill" at which the signal content becomes more dominated by the second time constant. This may, however, be a drawback to using this technique to extract the evoked response component. Depending on the time region of the cardiac response which is to be detected, the different time constants may dominate the measured signal. A typical time constant for polarization is 30 ms, and the detection window for the evoked response ranges from 5 ms to 50 ms following the stimulation pulse.

The previously-discussed VVI configuration shown in FIG. 1 represents a particularly difficult measurement situation. As noted above, the cardiac signal is sensed between the electrode tip in the ventricle, and the pacemaker housing. The stimulation amplitude is typically −5 V, and the electrode polarization has a beginning amplitude at approximately 10 percent of this value, which represents a relatively high electrode polarization.

Six test cases, respectively identifying different types of signals, are discussed below, wherein the test signals are obtained using the configuration shown in FIG. 1, but the sixth test case was structured to simulate atrial sensing.

In the following examples, signal processing in accordance with the principles of the present invention is undertaken using a first embodiment, shown in FIG. 12. As shown therein, stimulation and sensing take place between the tip electrode and the pacemaker can, serving as the indifferent electrode. The detected signal is supplied to a prefilter, which may be an anti-aliasing filter, typically a second order low pass filter with a 3 dB point at 250 Hz. Amplification can also take place in the prefilter. The output of the prefilter is then converted into digital form in an A/D converter, and samples are collected and stored in a signal buffer, during a data collection window set by the timing control.

The samples supplied from the signal buffer can, if desired, be pre-processed in a pre-processing stage. This pre-processing may include removal of constant (offset) levels, linear trends, and further filtering and/or differentiation of the signal.

The samples from the signal buffer (or the output of the pre-processing stage, if used) are supplied to a processing stage, wherein calculation of the autocorrelation function takes place in a calculation window. (If the pre-processing stage is used, the pre-processing therein also takes place during the calculation window). The calculation window is defined by the timing control.

The output of the processing stage is supplied to a normalize and difference unit, wherein the aforementioned normalization and difference-forming take place. Optional post processing can be undertaken on the difference signal in a post-processing stage. This post-processing, for example, could be differentiation of the signal or filtering.

The output of the normalize and difference unit (or the output of the post-processing stage, if used) is supplied to a detector which, in a detection window, analyzes the difference signal to determine whether an evoked response occurred. The detection window is also set by the timing control. The detector supplies an output to the pacing logic and control, which takes appropriate action in a known manner dependent on whether an evoked response was detected.

The first measurement situation which is simulated uses a measured signal consisting of a number of components: three different polarization-dependent exponential components, namely a fast component having an amplitude of 5 mV and a time constant of 0.2 ms, an intermediate part having an amplitude of 450 mV and a time constant of 30 ms, and a slow part having an amplitude of 45 mV and a time constant of 200 ms. The signal also includes a constant offset level of −5 mV and a linear trend of +10 mV/s.

Figure 13:
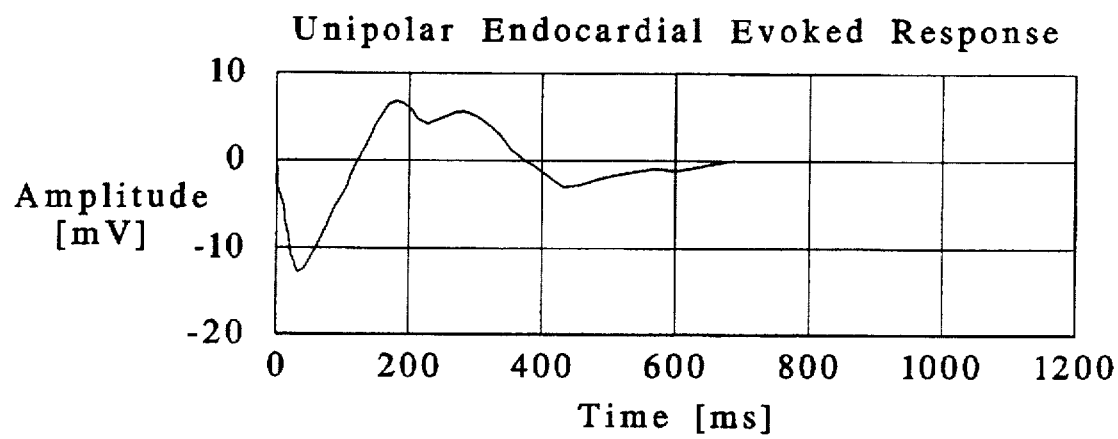
FIG. 13 shows a unipolar endocardial evoked response of the type which it is desired to detect, obtained from the literature.

The test signal shown in FIG. 13 used in this first example is obtained from the literature, from the article "Analysis of the Morphology of the Unipolar Endocardial Paced Evoked Response," Brouwer et al., PACE, Vol. 13, March 1990, pp. 302–313.

The curve shown in FIG. 13 is based on performed evoked response measurement using a large number of electrodes from different manufacturers. The signal was measured in a unipolar manner between a ventricular electrode tip and a pacemaker can. A three-phase stimulation pulse complex was used to achieve very low polarization. The curve in FIG. 13 thus shows the pure cardiac component of the signal, which it is desired to detect. A total of 103 electrodes were studied in the aforementioned article, with the primary objective being to detect the first minimum of the signal, which occurs 36 ms after the stimulation pulse.

As noted above, the total analyzed signal is the sum of the cardiac component and the polarization. The cardiac component in the atrium is much smaller than in the ventricle. An example is 15 mV in the ventricle and 2 mV in the atrium. Therefore, the presence of polarization is a bigger problem for an atrial electrode, and this situation is analyzed subsequently.

Figure 14:
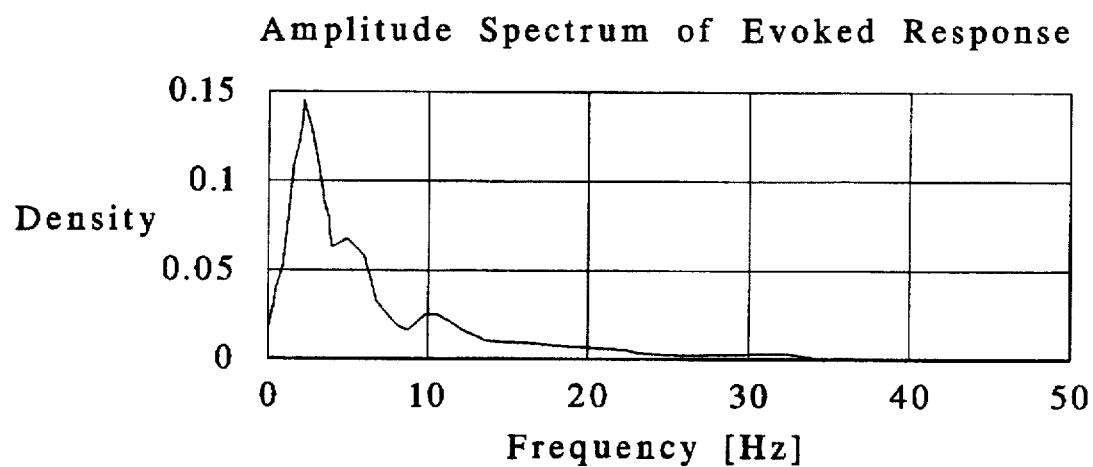
FIG. 14 shows the amplitude spectrum of the signal of FIG. 13.

The amplitude spectrum for the evoked response signal of FIG. 13 is shown in FIG. 14, wherein it can be seen that the maximum component is at 1.95 Hz.

Figure 15:
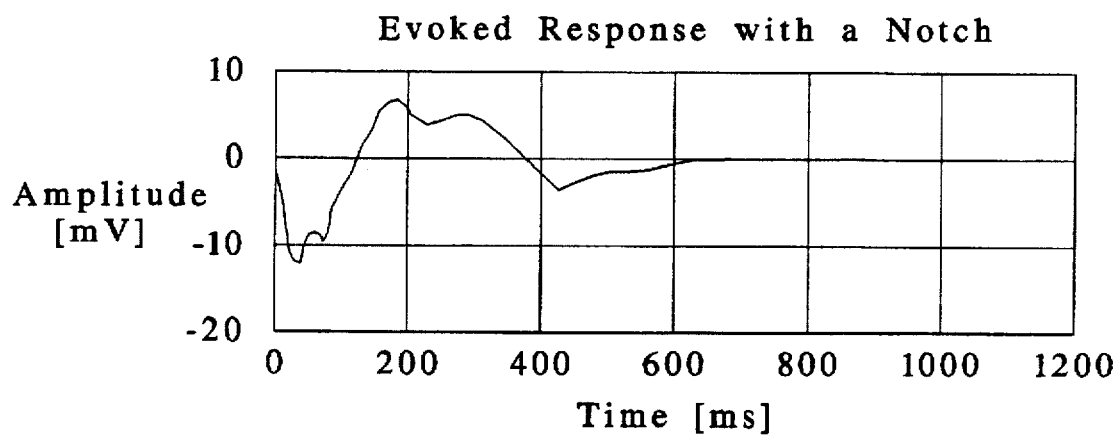
FIG. 15 shows an "ideal" form of a further type of evoked response which it is desired to detect, having a notch following the first minimum.

To further evaluate the detection algorithm, a small component is added to the signal at a time 45 ms following the stimulation pulse, appearing as a small notch after the first minimum. This signal is shown in FIG. 15, and constitutes a second test signal.

Figure 16:
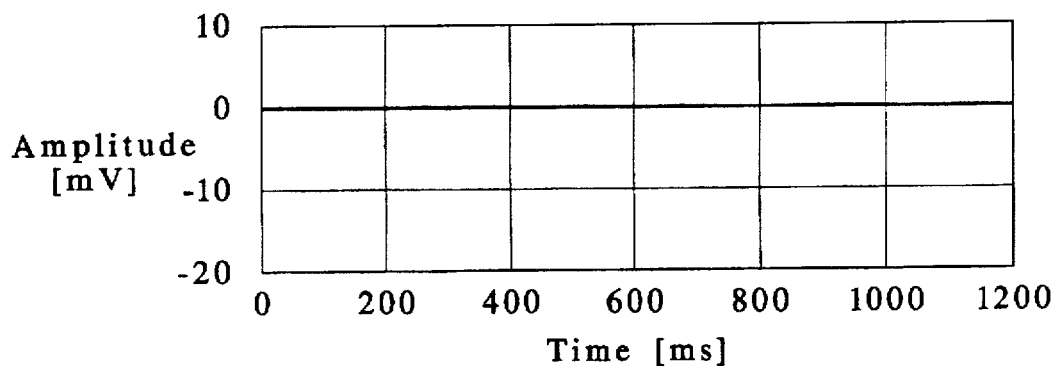
FIG. 16 shows a further type of evoked response, which is constantly zero, for use in explaining the invention.

A third test signal is shown in FIG. 16, which is an evoked response having a constant value of 0. The reason for using this third test signal is to enable residual components from the signal processing to be identified. In this case, the total signal being analyzed arises exclusively from the polarization.

Below follows the analysis for each of the first, second and third test signals. In the following analysis, it should be noted that the polarization has been selected to be very large, and it contains several components which present significant analytical difficulties. The measured signal is thus heavily corrupted, which may not normally be the case, but the examples show how the embodiment of the invention shown in FIG. 12 is able to provide reliable detection even under severe signal situations. The primary purpose of the method and apparatus is to extract a detectable evoked response signal, and to distinguish this situation from the case wherein no evoked response is present (FIG. 16).

Figure 17:
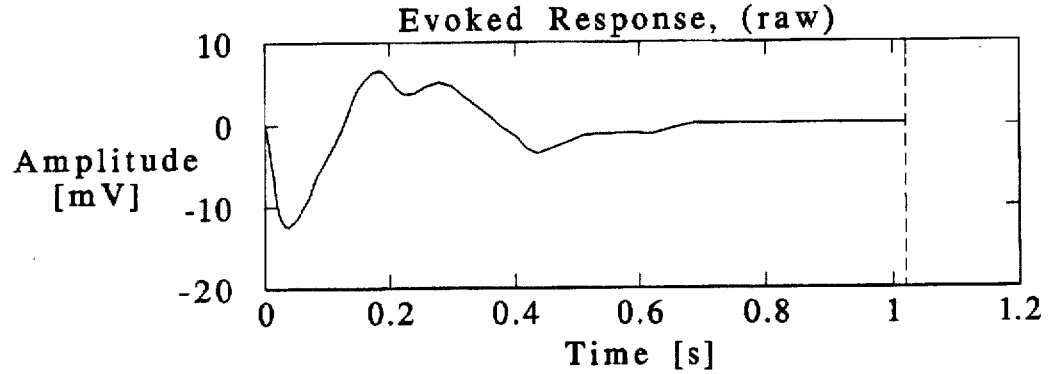
FIG. 17 shows a real, evoked response signal in raw form, generally corresponding to the form found in the literature shown in FIG. 13.
Figure 18:
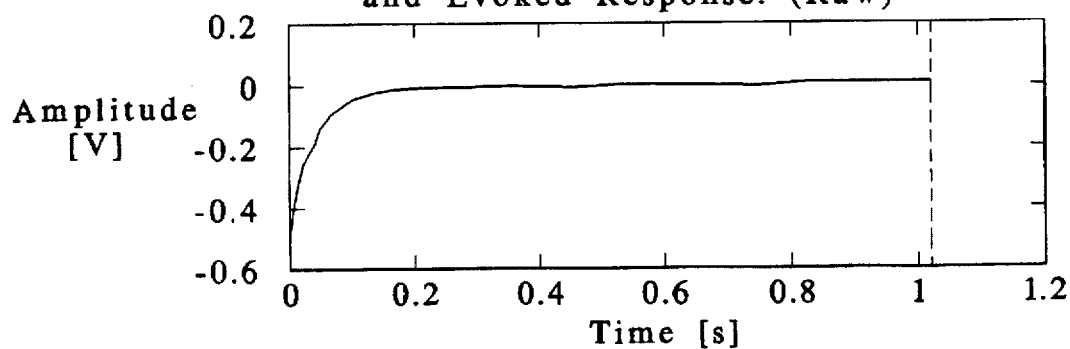
FIG. 18 shows the sum of polarization, biased, drift and evoked response components in the raw sensed signal.
Figure 19:
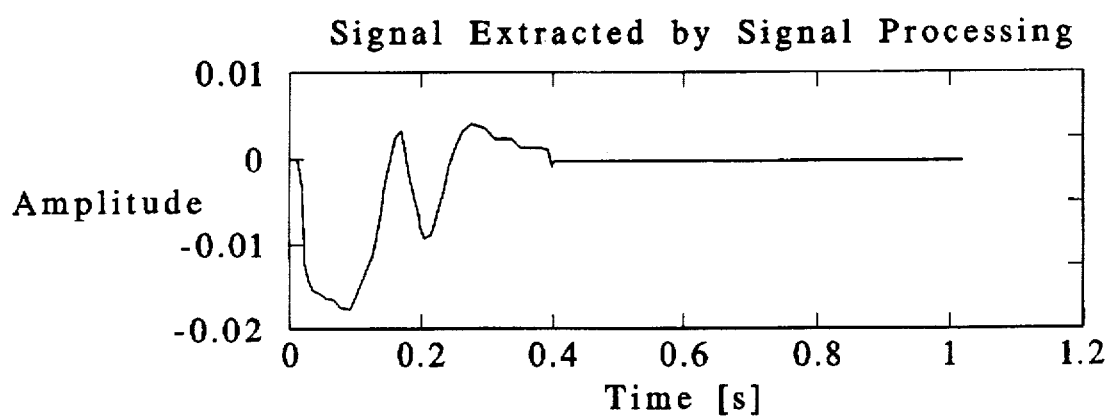
FIG. 19 shows the signal extracted by a signal processing in accordance with the invention.

For test signal 1 the raw evoked response signal is shown in FIG. 17, the sum of polarization, bias, drift and evoked response components in the raw signal is shown in FIG. 18, and the signal extracted by signal processing in accordance with the invention is shown in FIG. 19.

Figure 20:
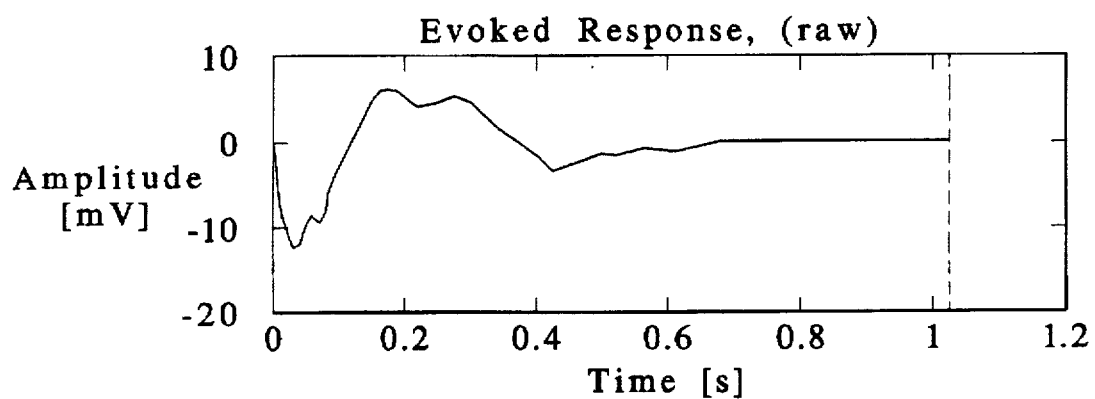
FIG. 20 shows a raw evoked response signal corresponding to the "ideal" version shown in FIG. 15.
Figure 21:
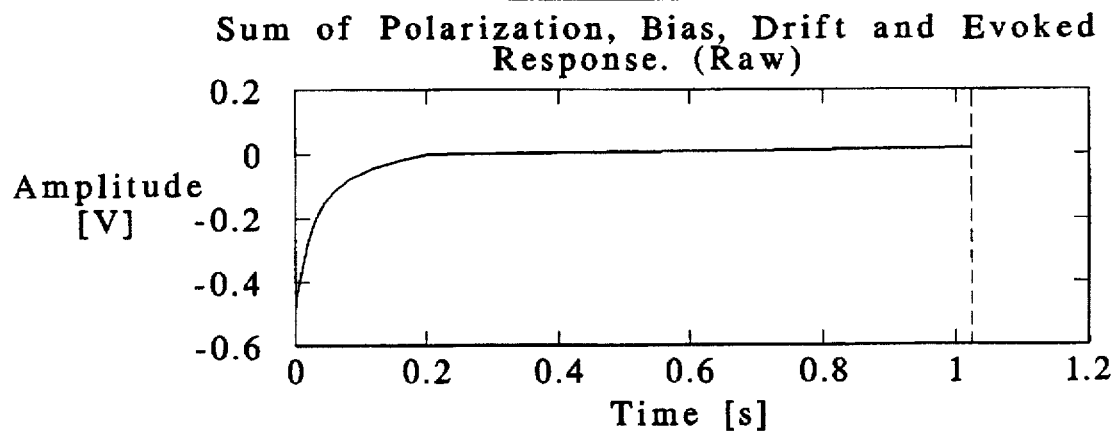
FIG. 21 shows the sum of polarization, bias, drift and evoked response components in the raw sensed signal.
Figure 22:
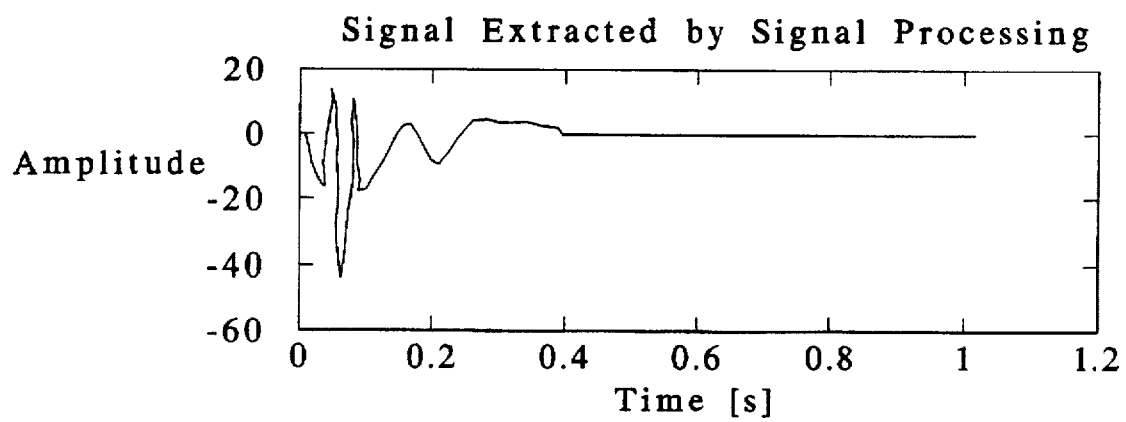
FIG. 22 shows the signal extracted by signal processing in accordance with the invention.

The unipolar evoked response having a notch in raw form is shown in FIG. 20, the sum of polarization, bias, drift and evoked response for this second test signal is shown in FIG. 21, and the signal extracted by signal processing in accordance with the invention is shown in FIG. 22.

Figure 23:
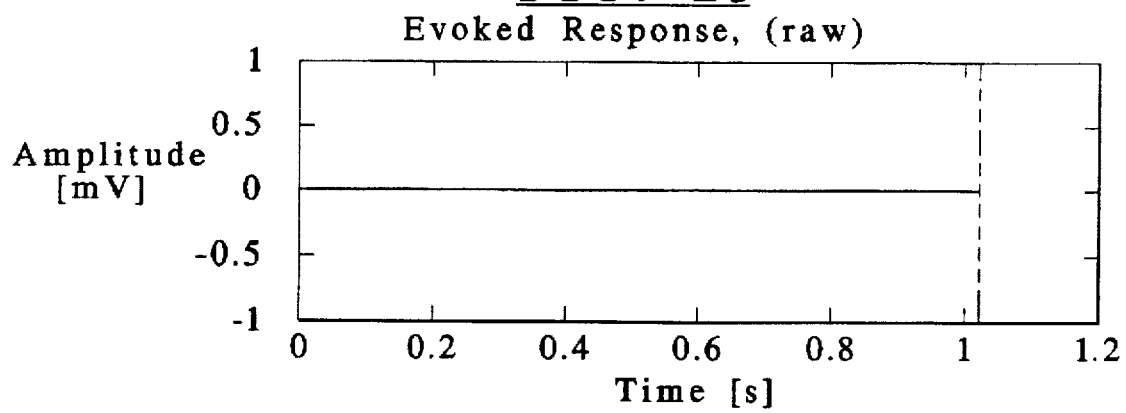
FIG. 23 shows a raw evoked response signal having a constant value of zero.
Figure 24:
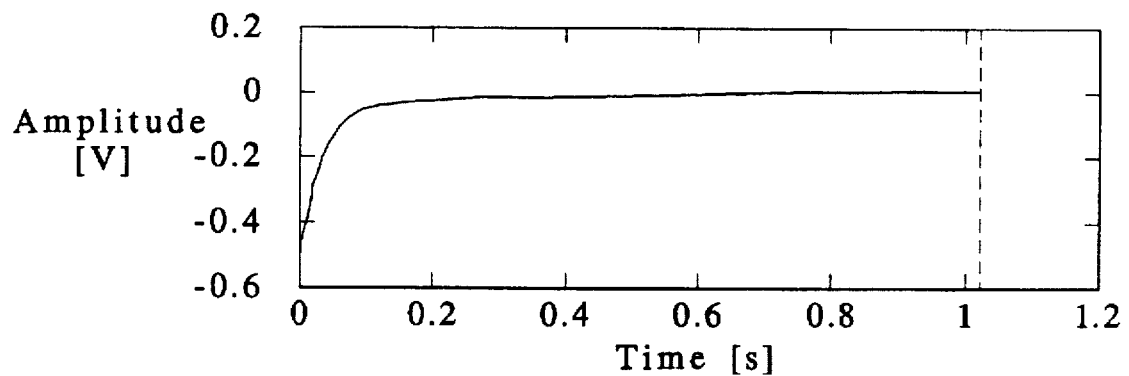
FIG. 24 shows the sum of polarization, bias, drift and evoked response in the raw sensed signal.
Figure 25:
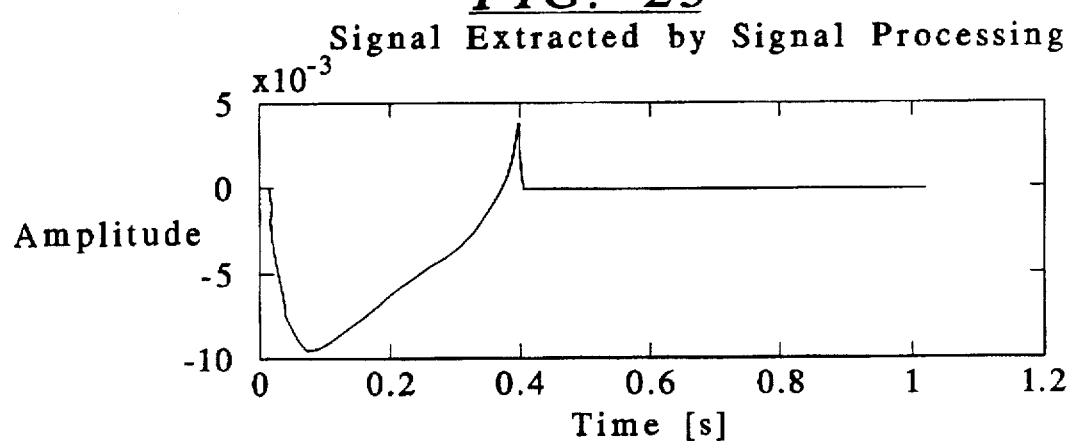
FIG. 25 shows the signal extracted by a signal processing in accordance with the invention.

A raw signal illustrating the absence of an evoked response is shown in FIG. 23, with the sum of polarization, bias, drift and evoked response components being shown in FIG. 24, and the signal extracted by signal processing in accordance with the invention is shown in FIG. 25.

In each of the test cases for the first, second and third test signals, the measured signal was first subjected to anti-aliasing filtering, and a data collection interval consisting of 400 ms after the stimulation pulse was used. The pre-processing used in this window was in the form of differentiation (although high pass filtering could alternatively be used). A time interval which is a portion of the data collection window was then used as the calculation window, this being a time interval of 10–400 ms after the stimulation pulse. The autocorrelation function is calculated in this window. Normalizing of both the pre-processed and processed signal was then performed by setting the maximum absolute value equal to one, also in the calculation window. The amplitude was shifted to zero at 10 ms before taking the difference. The resulting difference signal in each case is respectively shown in FIGS. 19, 22 and 25.

Test cases 4 and 5 are undertaken on a signal with less polarization; the polarization in test cases 4 and 5 was equal to the polarization in the preceding cases 1 through 3, divided by ten. The measured signal consists of components including three different polarization-dependent exponential parts, namely a fast part having an amplitude of 0.5 mV and a time constant of 0.2 ms, an intermediate part having an amplitude of 0.45 mV and a time constant of 30 ms, and a slow part having an amplitude of 4.5 mV and a time constant of 200 ms. The measured signal had a constant offset level of −0.5 mV and a linear trend of +1 mV/s. Signal processing was undertaken in the same manner as described above in connection with cases 1 through 3, however, a shorter time window was used; 200 ms instead of 400 ms.

Figure 26:
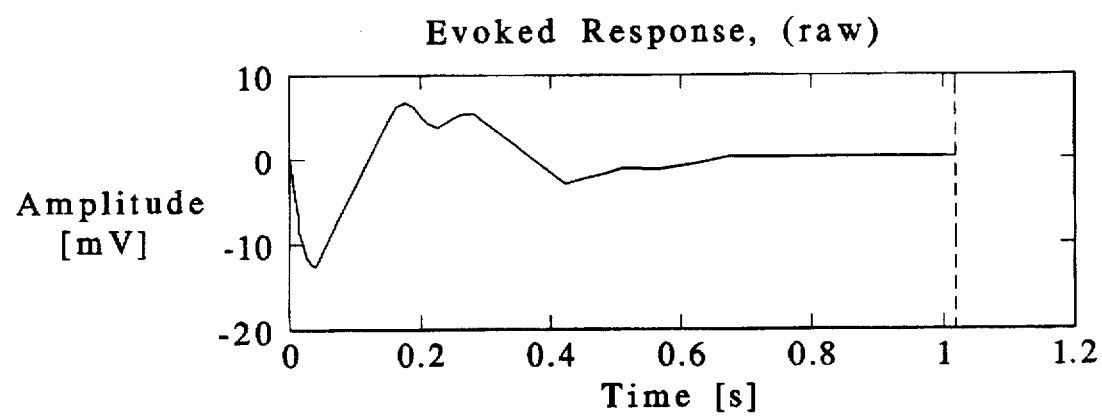
FIG. 26 shows a further evoked response signal, having a shorter time window which can be used when lower polarization exists in the ventricle.
Figure 27:
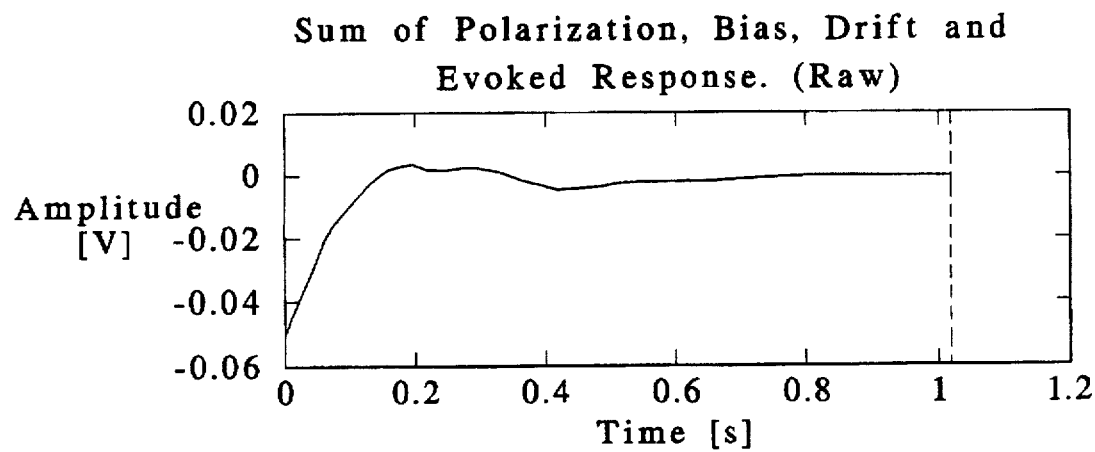
FIG. 27 shows the sum of polarization, bias, drift and evoked response components in the raw sensed signal.
Figure 28:
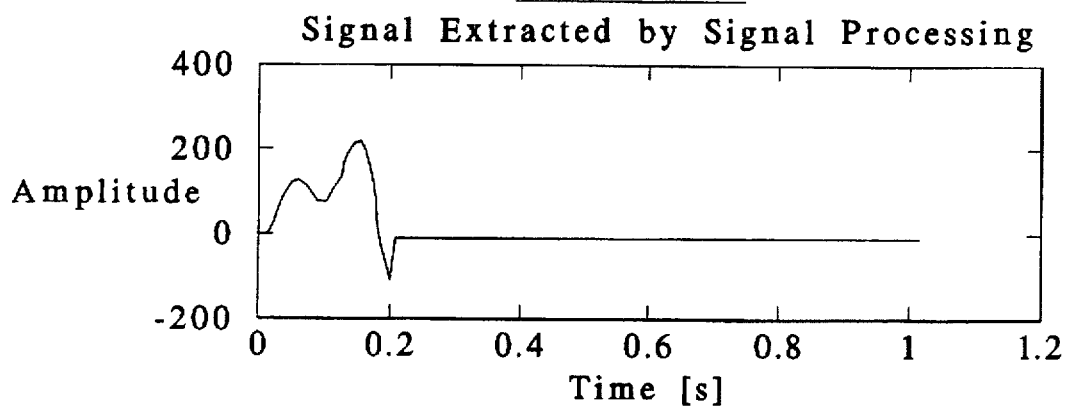
FIG. 28 shows the signal extracted by signal processing in accordance with the invention.
Figure 29:
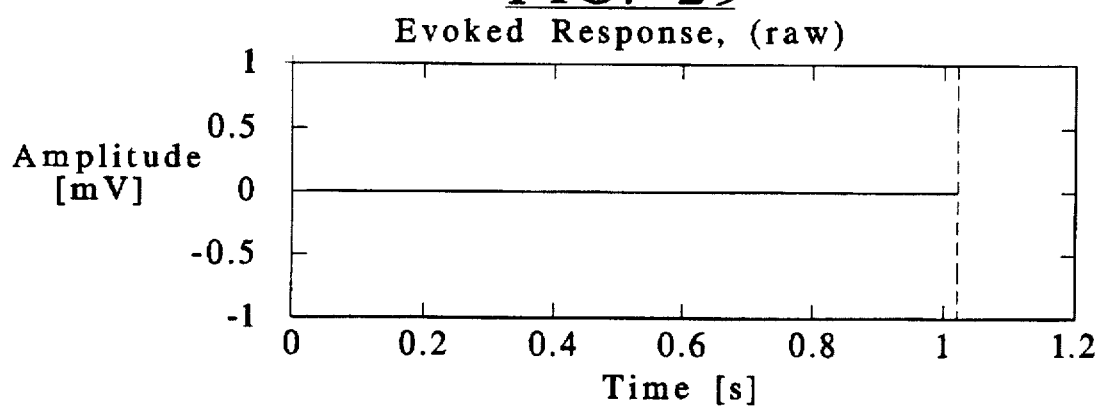
FIG. 29 shows another raw evoked response signal, having a value which is constantly zero, with a shorter time window, with lower polarization in the ventricle.

The raw evoked response signal for test case 4, with low polarization in the ventricle which allows a shorter time window to be used, is shown in FIG. 26 (such a situation exists as well for FIGS. 27–30 and 32). The sum of the polarization, bias, drift and evoked response components for the signal of FIG. 26 is shown in FIG. 27, and the result of signal processing in accordance with the invention is shown in FIG. 28. Again, unipolar sensing was used.

Figure 30:
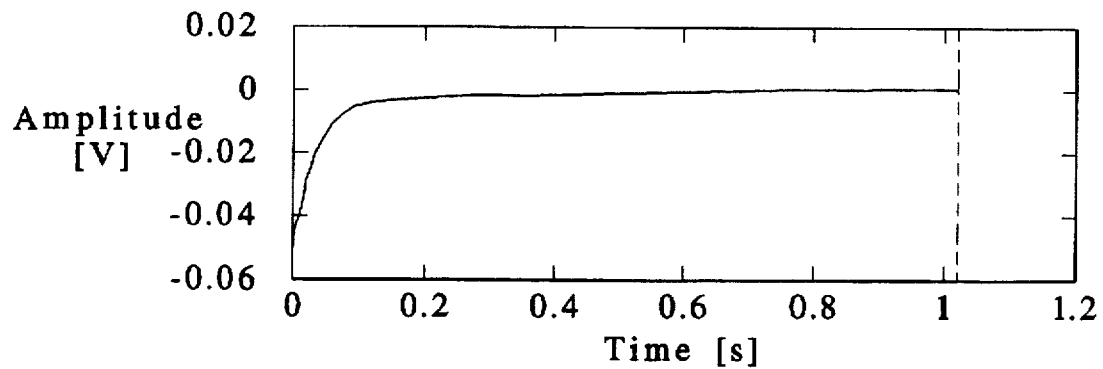
FIG. 30 shows the sum of polarization, bias, drift and evoked response components in the raw sensed signal.
Figure 31:
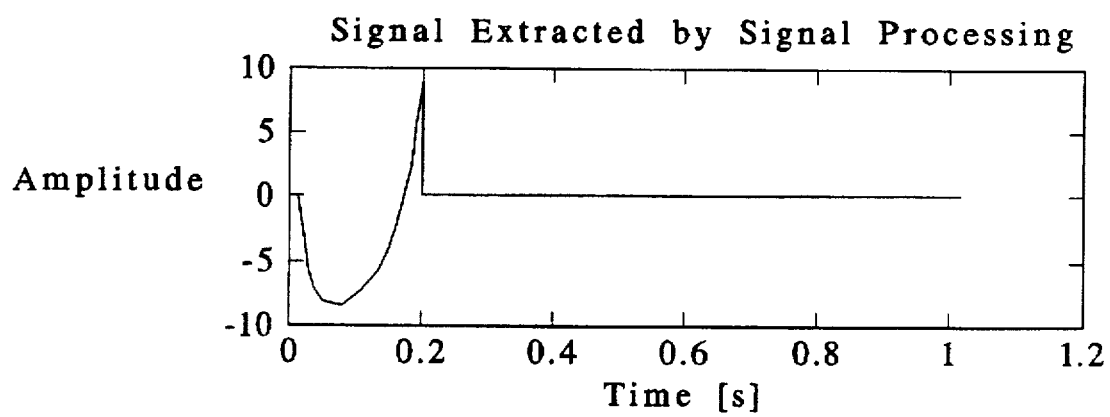
FIG. 31 shows the signal extracted by a signal processing in accordance with the invention.

For the fifth test case, the blank evoked response shown in FIG. 29 was used, again with low polarization in the ventricle and a shorter time window. The sum of the polarization, bias, drift and evoked response components in the raw signal is shown in FIG. 30, and the signal extracted by signal processing in accordance with the invention is shown in FIG. 31.

Lastly, test case 6 represents processing using a measured signal sensed in the atrium, with high polarization. The polarization components for the sixth test case are as in the first three test cases. The evoked response signal is scaled by a factor of 5, to simulate the situation in the atrium. The time window is 400 ms. The blank evoked response for this situation is the same as in the above-discussed third test case. (FIGS. 23–25)

Figure 34:
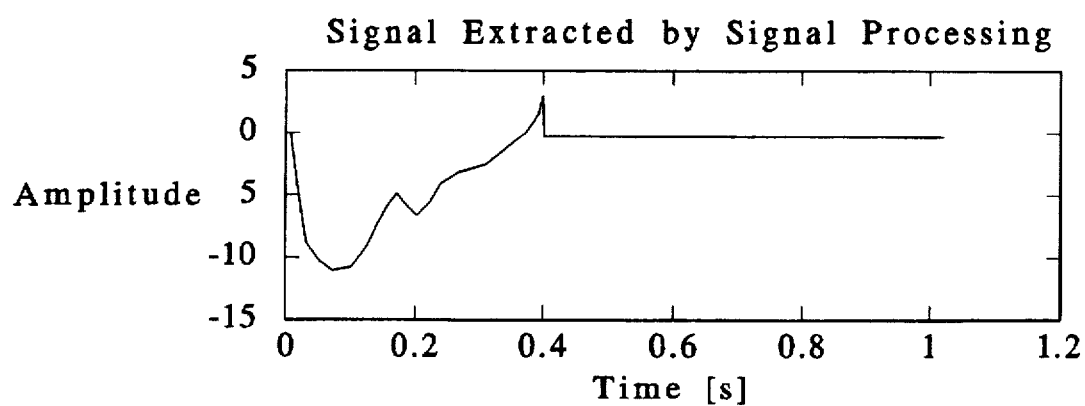
FIG. 34 shows the signal extracted by signal processing in accordance with the principles of the present invention.
Figure 32:
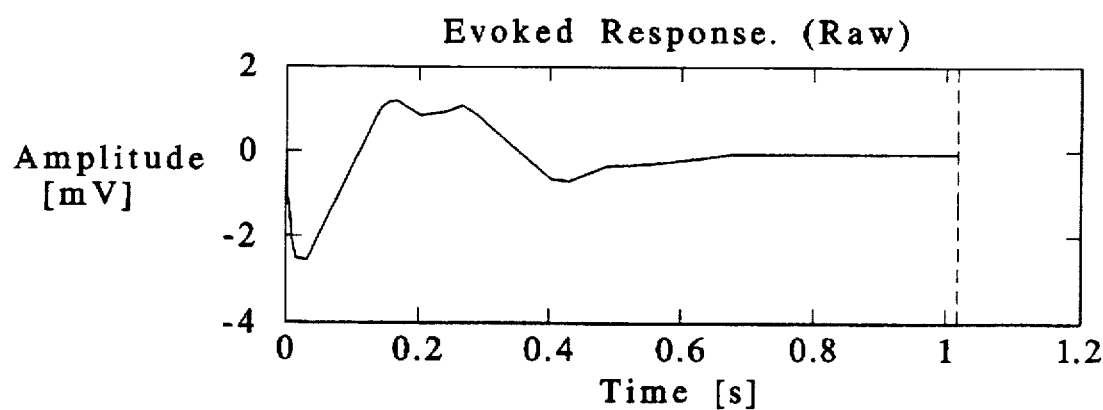
FIG. 32 shows an example of a raw evoked response arising without high polarization in the atrium.
Figure 33:
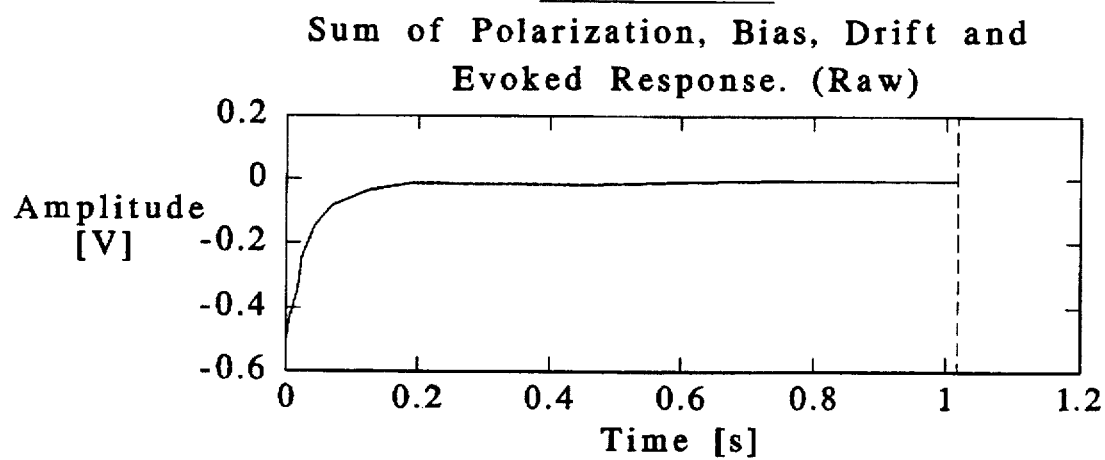
FIG. 33 shows the sum of polarization, bias, drift and evoked response components in the raw sensed signal.

FIG. 32 shows the raw evoked response signal for the sixth test case, FIG. 33 shows the sum of polarization, bias, drift and evoked response components, and FIG. 34 shows the signal extracted by signal processing in accordance with the invention, which can be compared to the blank case shown in FIG. 25.

As can be seen in all of the above test cases, the signal extracted by signal processing in accordance with the invention is easily distinguishable from the signal which is extracted in the absence of an evoked response (blank evoked response), and therefore detection of the presence of an evoked response can be easily undertaken.

Figure 12:
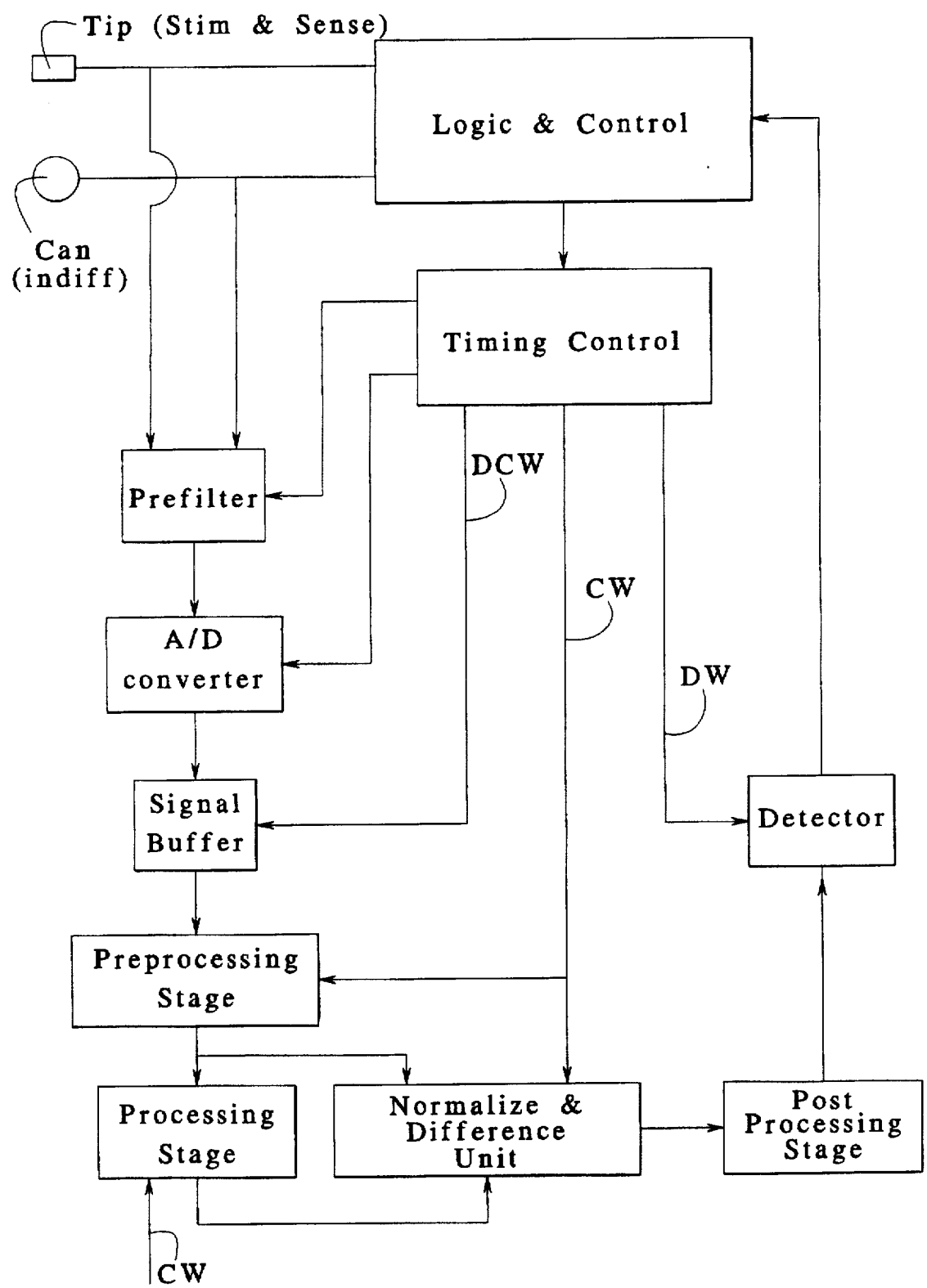
FIG. 12 is a schematic block diagram of a first embodiment of an apparatus for extracting the evoked response component from a sensed cardiac signal constructed and operating in accordance with the principles of the present invention.

As noted above, the signal processing embodiment shown in FIG. 12 is best suited for implementation using a microprocessor, but the calculations therein are not conducted in real time. An embodiment of the invention for real time analysis, which permits an analysis result to be obtained in time to generate a back-up pulse, if necessary, is shown in FIG. 35 in block diagram form, and in more detail in FIG. 36.

Figure 35:
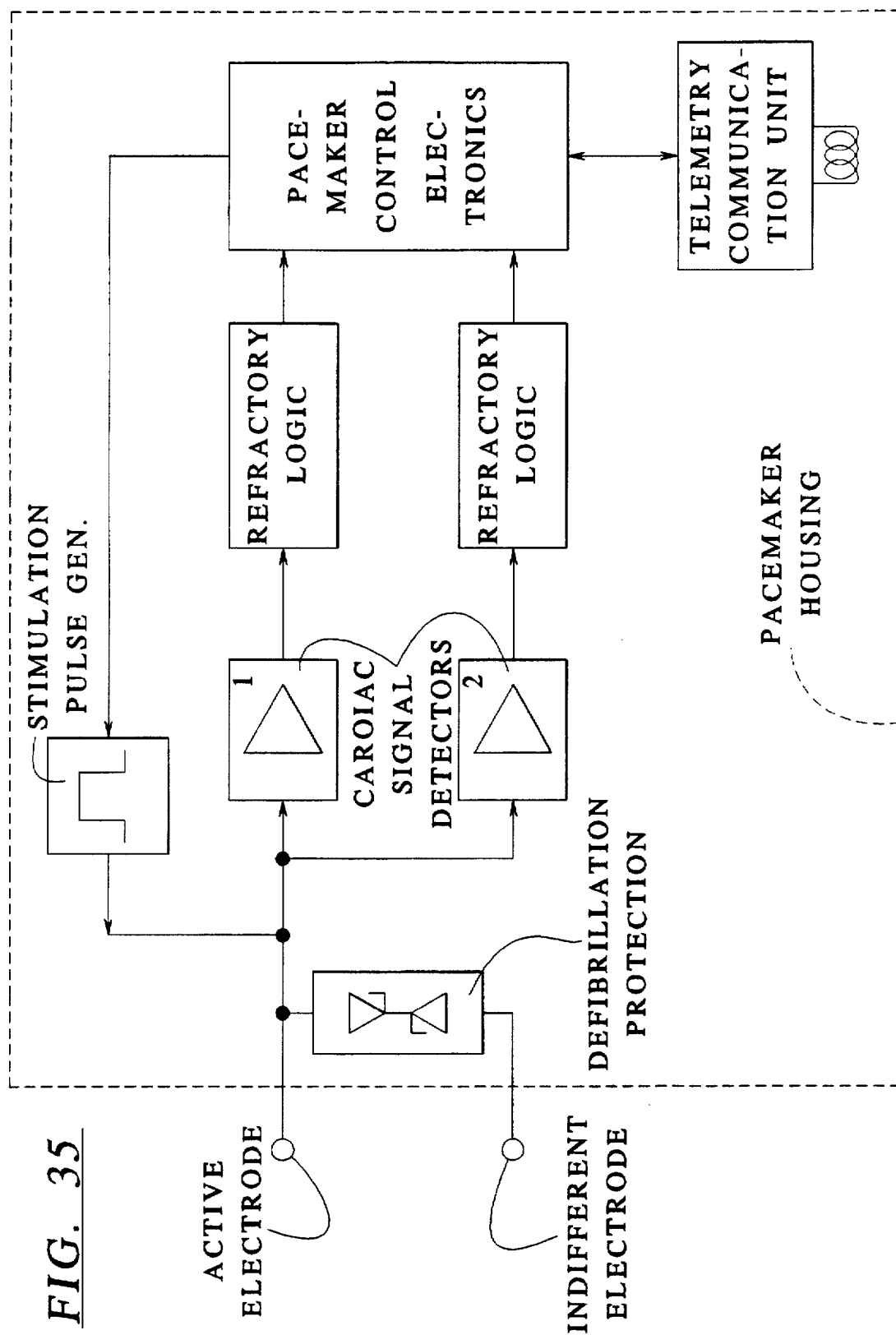
FIG. 35 is a circuit diagram showing a second embodiment of an apparatus for extracting an evoked response component from a sensed cardiac signal constructed and operating in accordance with the principles of the present invention.

As shown in FIG. 35, sensing takes place between an active electrode and an indifferent electrode, such as a tip electrode disposed in the ventricle as the active electrode, and the pacemaker housing as the indifferent electrode. The active electrode and the indifferent electrodes are connected across a high-voltage protection stage, as defibrillation protection, to protect the remainder of the pacemaker circuitry from the high voltages which arise in the event of defibrillation. In the example shown in FIG. 35, this stage includes a Zener diode, but a thyristor circuit is also suitable. The circuitry shown in FIG. 35 includes a standard stimulation pulse generator, which emits stimulation pulses via the active electrode and the indifferent electrode. Following the emission of a stimulation pulse, the pacemaker control electronics switches over to operation of the pacemaker in a sensing mode, with sensed (measured) cardiac signals, including the aforementioned polarization component, being received via cardiac signal detectors 1 and 2. Each detector 1 and 2 has refractory logic connected to its output, the outputs of the two refractory logic stages being supplied to the pacemaker control electronics. Only one detector is necessary to practice the invention, but using more than one detector increases the detection probability and/or permits different types of heart signals to be protected. The pacemaker control electronics communicates in a known manner with an external programmer (not shown) via a telemetry communication unit.

The cardiac signal detector 1 can either be dedicated for evoked response detection, or both for evoked response and spontaneous cardiac signal detection. In the first case, heart signal detector 2 is then used for spontaneous detection, in the second case heart signal detector 2 is not needed.

Figure 36:
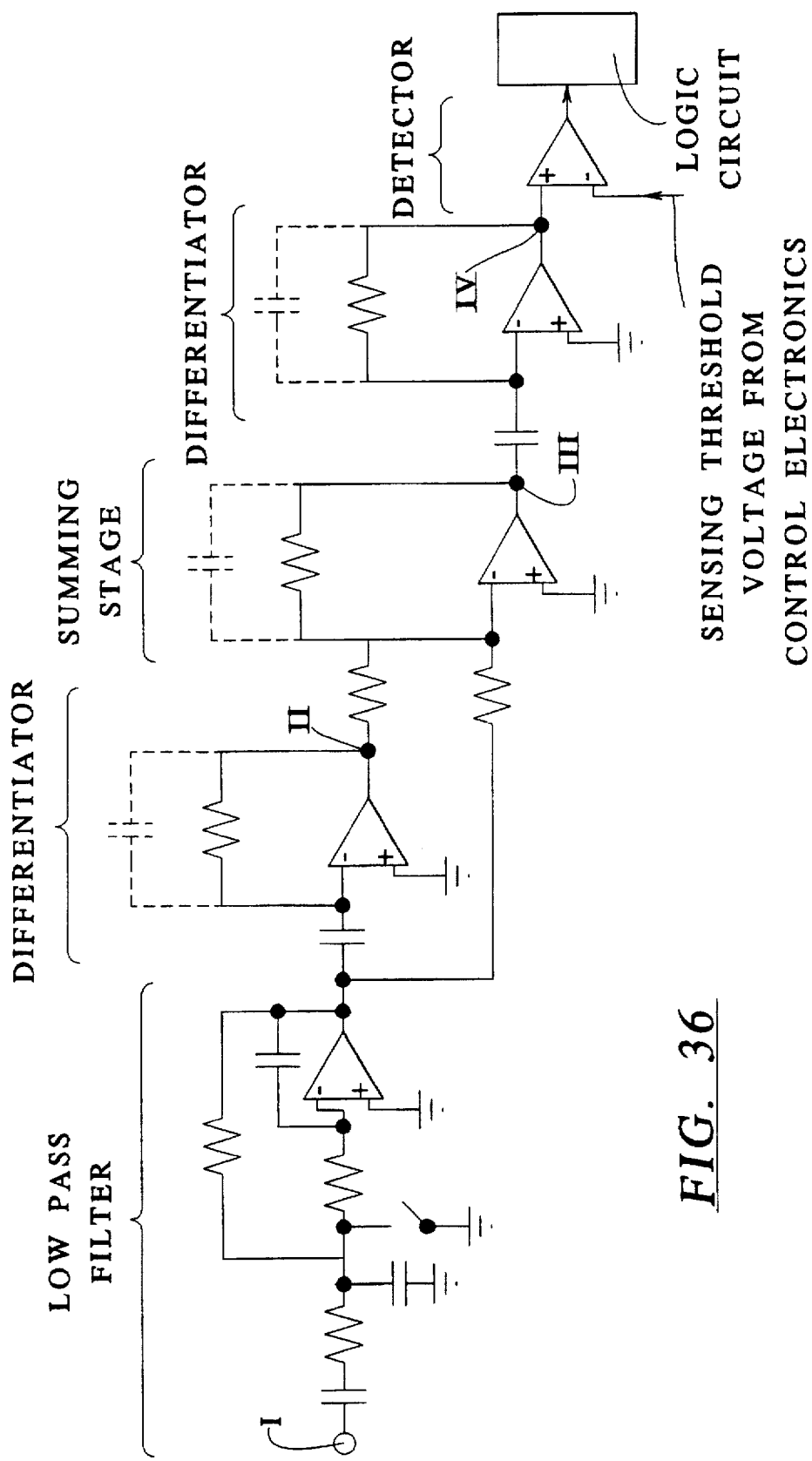
FIG. 36 shows circuit details of the embodiment of FIG. 35.

FIG. 36 shows the details of the cardiac signal detectors 1 and 2, which are identical. Each detector has a decoupling capacitor immediately following the input, which also serves a high pass filter. This is followed by a low pass filter stage, which also includes a zeroing switch, which is closed during the emission of a stimulation pulse. The low pass filter stage is followed by a differentiator stage, wherein the first derivative of the output of the low pass filter is obtained. The first derivative is supplied to a summing stage, together with the output of the low pass filter, which is supplied directly thereto, bypassing the differentiator stage. The first derivative and the original signal are added in the summing stage, and the output is differentiated in another differentiator stage. The output of the second differentiated stage is then level detected, by comparison against a sensing threshold voltage which is set by the control electronics. This level can be set by means of telemetry communication with the extracorporeal programmer. The output of the detector stage is supplied to the pacing logic, which is contained in the pacemaker control electronics.

Figure 37:
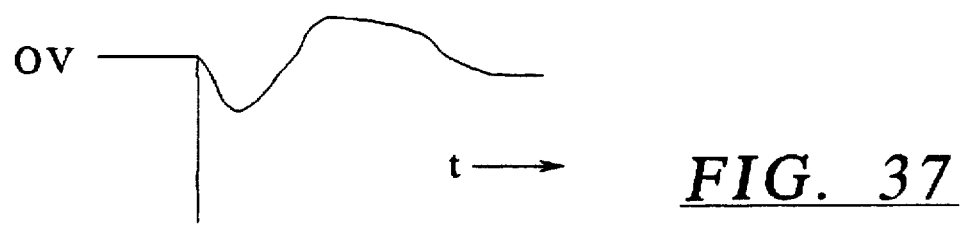
FIG. 37 shows the uninfluenced evoked response signal at location I in FIG. 36.
Figure 38:
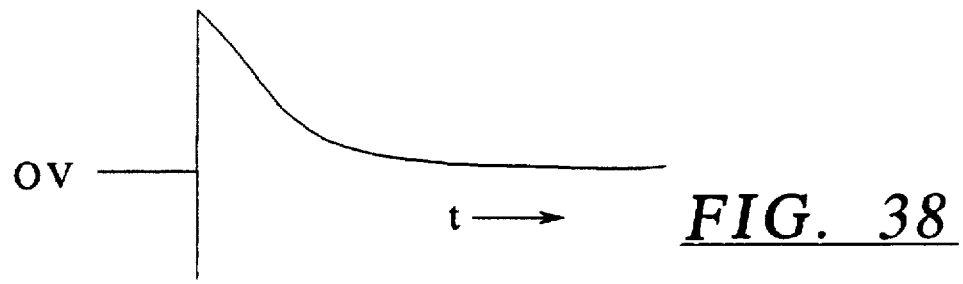
FIG. 38 shows the polarization signal at circuit location I in FIG. 36.
Figure 39:
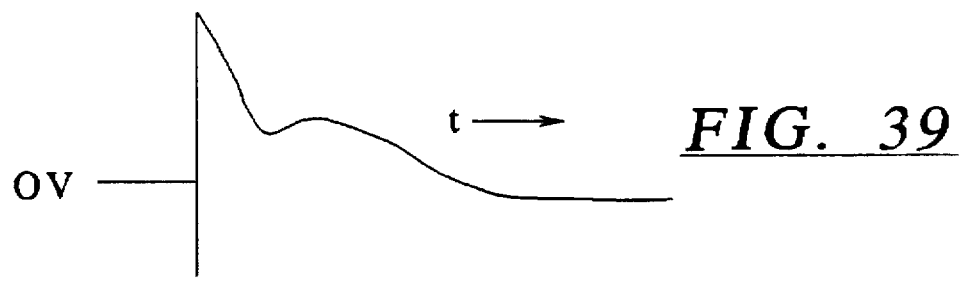
FIG. 39 shows the combined evoked response and polarization signal at location I in FIG. 36.
Figure 40:
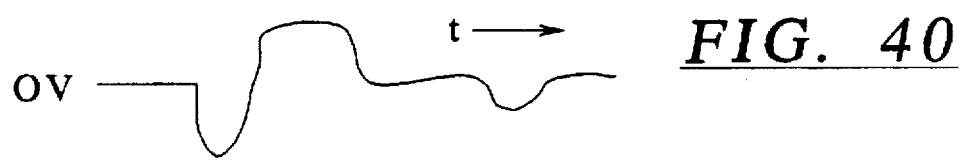
FIG. 40 shows the differentiated evoked response signal at location II in FIG. 36.
Figure 41:
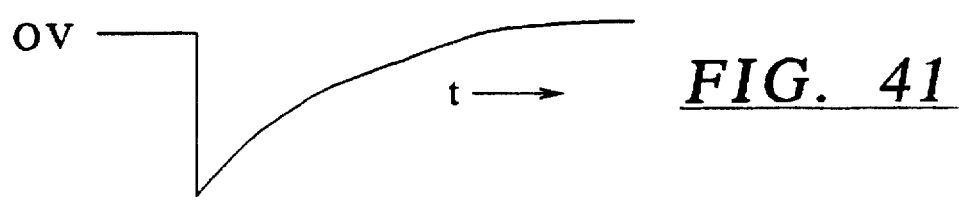
FIG. 41 shows the differentiated polarization signal at location II in FIG. 36.
Figure 42:
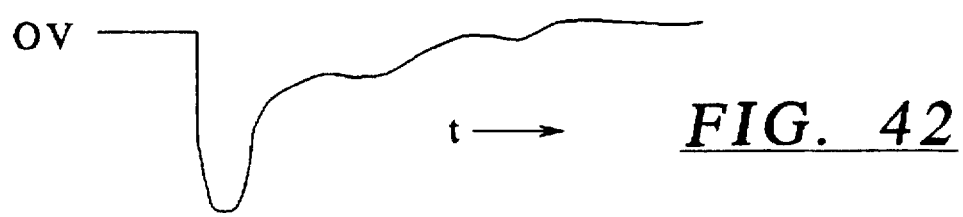
FIG. 42 shows the differentiated evoked response and polarization signal at location II in FIG. 36.

The uninfluenced evoked response signal, the overshadowing polarization signal, and the combined evoked response and polarization signal at location I of FIG. 36 are respectively shown in FIGS. 37, 38 and 39. The differentiated evoked response signal, the differentiated polarization signal, and the differentiated combination of the evoked response and polarization, as are present at location II in FIG. 36, are respectively shown in FIGS. 40, 41 and 42.

Figure 43:
FIG. 43 shows the sum of the original and differentiated evoked response signal at location III in FIG. 36.
Figure 44:
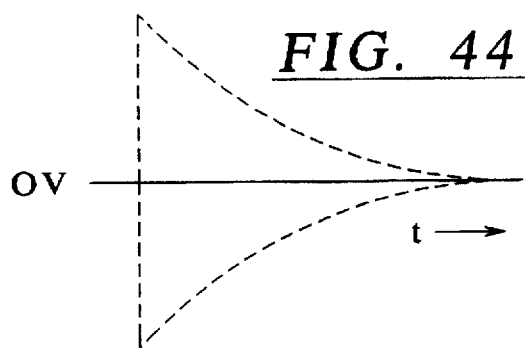
FIG. 44 shows the sum of the original and differentiated polarization signal at location III in FIG. 36.
Figure 45:
FIG. 45 shows the sum of the original and differentiated evoked response signal with polarization at location III in FIG. 36.
Figure 49:
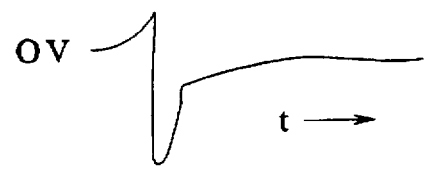
FIG. 49 shows the sum of the original and differentiated heart signals.
Figure 46:
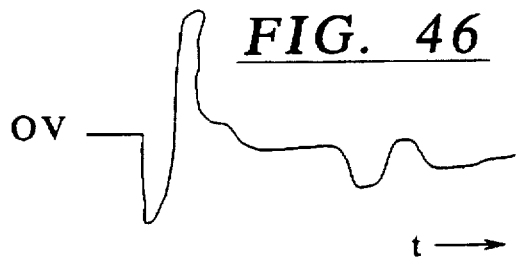
FIG. 46 shows further signal processing with differentiating before level detection at location IV FIG. 36.

The sum of the original and differentiated evoked response signal, the sum of the original and differentiated polarization signal, and the sum of the original and differentiated evoked response signal with polarization, as occur at location III in FIG. 36, are respectively shown in FIGS. 43, 44 and 45. The result of the further signal processing (i.e., differentiating before detection), as occurs at location IV in FIG. 36 is shown in FIG. 46, with an exemplary detecting level shown therein. This detecting level is set in the subsequent detector stage, as described above, by the control electronics. A signal such as that shown in FIG. 46, which has a peak which exceeds the detecting level, is registered as containing an evoked response. Other detection techniques, as are well-known to those of ordinary skill in the art, can be used instead of, or addition to, level detecting.

Figure 47:
FIG. 47 shows a spontaneous heart signal generated without the assistance of a stimulation pulse, which produces a polarization component.
Figure 48:
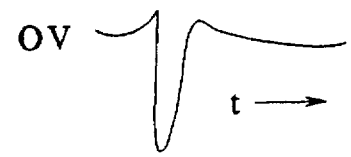
FIG. 48 shows the differentiated spontaneous heart signal.
Figure 50:
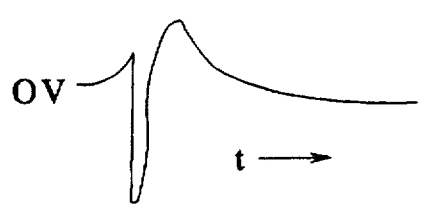
FIG. 50 shows the effect of further signal processing with differentiation on the signal of 49, before level detection.

For comparison purposes, FIG. 47 shows a spontaneous heart signal as it appears at location I in FIG. 36, FIG. 48 shows the differentiated spontaneous cardiac signal as it appears at location II, FIG. 48 shows the sum of the original and differentiated cardiac signals as the sum appears at III, and FIG. 50 shows the result of further signal processing with differentiation, before detection, as occurs at location IV. Again, the detecting level has been entered in FIG. 50.

Instead of the arrangement shown in FIG. 36, signal processing can be undertaken with other techniques, such as the switched capacitor technique, wherein signal processing is performed by sampling and transferring charges between capacitors on an integrated circuit. With the switched capacitor technique, differentiation and summing are easy to implement. Processing is undertaken with a sampling frequency which is higher than the most rapid variation of interest in the signal. This means that a suitable sampling frequency is between 500 and 1500 Hz. The result is then a voltage level which can be compared in a detector (comparator) circuit.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a method for suppressing electrode polarization components in a sensed cardiac signal, wherein a heart is stimulated by delivering an electrical signal to said heart which, if successful, produces an evoked response by said heart, wherein electrical activity is sensed in said heart after delivering said electrical signal and obtaining a sensed cardiac signal including a polarization component, and if stimulation was successful, an evoked response component, the improvement comprising:

(a) applying an autocorrelation function to said sensed cardiac signal to obtain an autocorrelated signal;

(b) normalizing said sensed cardiac signal and said autocorrelated signal relative to each other; and (c) forming a difference between the normalized sensed cardiac signal and the normalized autocorrelated signal and thereby extracting said evoked response component if present.

2. A method as claimed in claim 1 wherein sensing is undertaken in a data collection window, and wherein step (a) comprises applying said autocorrelation function in a calculation window which is a portion of said data collection window.

3. A method as claimed in claim 2 comprising the additional step of anti-aliasing filtering said sensed cardiac signal and thereafter selecting said data collection window.

4. A method as claimed in claim 2 comprising the additional step of pre-processing said sensed cardiac signal in said data collection window to obtain a pre-processed sensed cardiac signal, and using said pre-processed sensed cardiac signal as said sensed cardiac signal in steps (a) and (b).

5. A method as claimed in claim 4 wherein the step of pre-processing said sensed cardiac signal comprises taking a first derivative of said sensed cardiac signal.

6. A method as claimed in claim 4 wherein the step of preprocessing said sensed cardiac signal comprises high pass filtering said sensed cardiac signal.

7. A method as claimed in claim 1 wherein step (b) comprises setting respective maxima of said sensed cardiac signal and said autocorrelated signal to a common value.

8. A method as claimed in claim 7 wherein said common value is one.

9. In an apparatus for suppressing electrode polarization components in a sensed cardiac signal, including means for stimulating a heart by delivering an electrical signal to said heart which, if successful, produces an evoked response by said heart, means for sensing electrical activity in said heart after delivering said electrical signal and obtaining a sensed cardiac signal including a polarization component, and if stimulation was successful, an evoked response component, the improvement comprising:

means for applying an autocorrelation function to said sensed cardiac signal to obtain an autocorrelated signal;

means for normalizing said sensed cardiac signal and said autocorrelated signal relative to each other; and means for forming a difference between the normalized sensed cardiac signal and the normalized autocorrelated signal and thereby extracting said evoked response component, if present.

10. An apparatus as claimed in claim 9 wherein said means for sensing comprises means for sensing in a data collection window, and wherein said means for applying an autocorrelation function comprises means for applying said autocorrelation function in a calculation window which is a portion of said data collection window.

11. An apparatus as claimed in claim 10 further comprising an anti-aliasing filter to which said sensed cardiac signal is supplied.

12. An apparatus as claimed in claim 10 further comprising means for pre-processing said sensed cardiac signal in said data collection window to obtain a pre-processed sensed cardiac signal, and wherein said means for applying an autocorrelation function and said means for normalizing each operate on said pre-processed sensed cardiac signal as said sensed cardiac signal.

13. An apparatus as claimed in claim 12 wherein said means for pre-processing comprises means for differentiating said sensed cardiac signal.

14. An apparatus as claimed in claim 12 wherein said means for pre-processing comprises a high pass filter.

15. An apparatus as claimed in claim 9 wherein said means for normalizing comprises means for identifying respective maxima in said sensed cardiac signal and said autocorrelated signal, and for setting said maxima to a common value.

16. An apparatus as claimed in claim 15 wherein said means for normalizing comprises means for setting each of said maxima to a value of one.

17. An apparatus as claimed in claim 9 wherein said means for sensing includes a unipolar electrode.

18. In a method for suppressing electrode polarization components in a sensed cardiac signal, wherein a heart is stimulated by delivering an electrical signal to said heart which, if successful, produces an evoked response by said heart, wherein electrical activity is sensed in said heart after delivering said electrical signal and obtaining a sensed cardiac signal including a polarization component, and if stimulation was successful, an evoked response component, the improvement comprising:

(a) low pass filtering said sensed cardiac signal to obtain a low pass filtered signal;

(b) differentiating said low pass filtered signal to obtain a differentiated signal;

(c) adding said low pass filtered signal and said differentiated signal to obtain a sum;

(d) differentiating said sum to obtain a differentiated sum; and (e) analyzing said differentiated sum to identify at least one signal parameter therein indicative of a presence of an evoked response in said sensed cardiac signal.

19. A method as claimed in claim 18 wherein step (e) comprises means for comparing said differentiated sum to a predetermined signal level, and for detecting a presence of an evoked response in said sensed cardiac signal if said at least one signal parameter exceeds said predetermined signal level.

20. In an apparatus for suppressing electrode polarization components in a sensed cardiac signal, including means for stimulating a heart by delivering an electrical signal to said heart which, if successful, produces an evoked response by said heart, means for sensing electrical activity in said heart after delivering said electrical signal and obtaining a sensed cardiac signal including a polarization component, and if stimulation was successful, an evoked response component, the improvement comprising:

means for low pass filtering said sensed cardiac signal to obtain a low pass filtered signal;

means for differentiating said low pass filtered signal to obtain a differentiated signal;

means for adding said low pass filtered signal and said differentiated signal to obtain a sum;

means for differentiating said sum to obtain a differentiated sum; and means for analyzing said differentiated sum to identify at least one signal parameter therein indicative of a presence of an evoked response in said sensed cardiac signal.

21. An apparatus as claimed in claim 19 wherein said means for analyzing comprises means for comparing said differentiated sum to a predetermined signal level, and for identifying a presence of an evoked response in said sensed cardiac signal if said at least one signal parameter exceeds said predetermined signal level.

* * * * *